US00PP18484P3

(12) United States Plant Patent
Zerr

(10) Patent No.: US PP18,484 P3
(45) Date of Patent: Feb. 12, 2008

(54) POINSETTIA PLANT NAMED 'FISMARS MARBLE'

(50) Latin Name: ***Euphorbia pulcherrima* (Willd. Ex Klotzsch)**
Varietal Denomination: Fismars Marble

(75) Inventor: Katharina Zerr, Höhr-Grenzhausen (DE)

(73) Assignee: Florfis AG, Binningen (CH)

( * ) Notice: Subject to any disclaimer, the term of this patent is extended or adjusted under 35 U.S.C. 154(b) by 136 days.

(21) Appl. No.: 11/346,125

(22) Filed: Feb. 2, 2006

(65) Prior Publication Data

US 2007/0180593 P1 Aug. 2, 2007

(51) Int. Cl.
*A01H 5/00* (2006.01)

(52) U.S. Cl. ..... Plt./303
(58) Field of Classification Search ..... Plt./303
See application file for complete search history.

(56) References Cited

U.S. PATENT DOCUMENTS

PP8,833 P * 7/1994 Fruehwirth ..... Plt./303
PP13,400 P2 * 12/2002 Dummen ..... Plt./303
PP14,977 P2 * 7/2004 Zerr ..... Plt./307

OTHER PUBLICATIONS

UPOV ROM GTITM Computer Database, GTI Jouve Retrieval Software 2006/05, Citations for 'Fismars Marble'.*

* cited by examiner

*Primary Examiner*—Wendy Haas
(74) *Attorney, Agent, or Firm*—Jondle & Associates P.C.

(57) ABSTRACT

A new Poinsettia plant particularly distinguished by medium to large size, bi-colored pink and cream bracts, with dark green foliage, ovate leaves with nearly no lobes, medium flowering response and a compact to medium size, round plant habit, is disclosed.

2 Drawing Sheets

Genus and species: *Euphorbia pulcherrima* (Willd. Ex Klotzsch).
Variety denomination: 'Fismars Marble'.

BACKGROUND OF THE NEW PLANT

The present invention comprises a new and distinct cultivar of poinsettia plant, botanically known as *Euphorbia pulcherrima* (Willd.) and hereinafter referred to by the cultivar name 'Fismars Marble'. The new cultivar is the result of an induced mutation in the poinsettia plant 'Fismars' (U.S. Plant Pat. No. 14,977) made in the year 2003 in Ahrensburg, Germany.

In May 2003, young plants of 'Fismars' were irradiated in Ahrensburg, Germany. The treated plants were grown in Hillscheid, Germany, and were propagated by shoot tip cuttings. The resulting plants were screened for positive mutations and examined during the flowering period in winter 2004/2005. Among these plants, a pink-flowered plant was selected and asexually multiplied for further examination in 2005.

The new cultivar was created in 2003 in Ahrensburg, Germany and has been asexually reproduced repeatedly by vegetative cuttings in Hillscheid, Germany over a two-year period. 'Fismars Marble' has not been observed under all possible environmental conditions. The present invention has been found to retain its distinctive characteristics through successive asexual propagations.

Plants Breeder's Rights for this cultivar were applied for in Europe on Feb. 9, 2005 and in Canada on Mar. 18, 2005.

SUMMARY OF THE INVENTION

The following are the most outstanding and distinguishing characteristics of this new cultivar when grown under normal horticultural practices in Hillscheid, Germany.

1. Bi-colored bracts with a pink center and a cream colored margin;
2. Medium to large size inflorescence;
3. Dark green foliage with ovate leaves that have nearly no lobes;
4. Compact to medium size, rounded plant habit; and
5. A medium flowering response.

DESCRIPTION OF PHOTOGRAPHS

This new poinsettia plant is illustrated by the accompanying photographs which show overall plant habit including blooms, buds, and foliage of the plant; the colors shown are as true as can be reasonably obtained by conventional photographic procedures. The photographs are of a whole plant about 18-weeks old and in full flower, grown in a greenhouse in Hillscheid, Germany, in mid January of 2006.

DESCRIPTION OF THE NEW CULTIVAR

Figure 1:
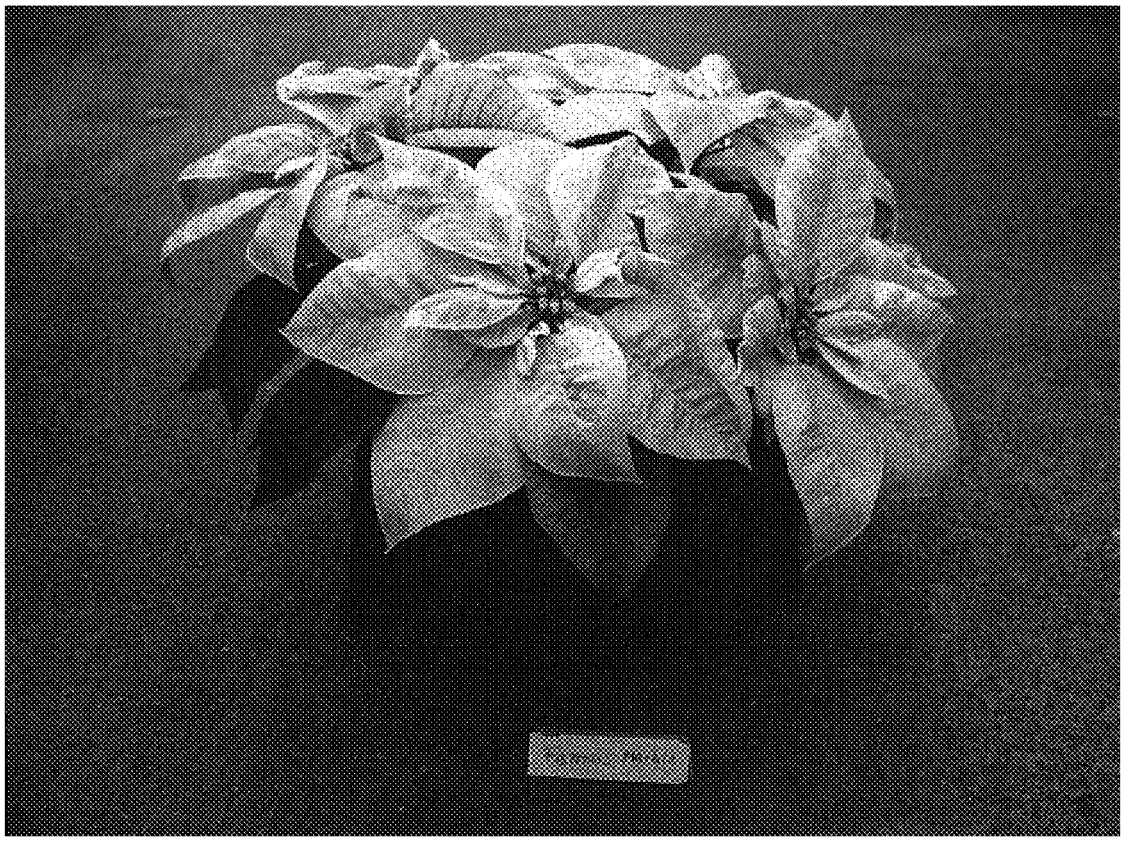
FIG. 1 shows the overall plant habit, including blooms, buds, mature foliage, and plant habit.
Figure 2:
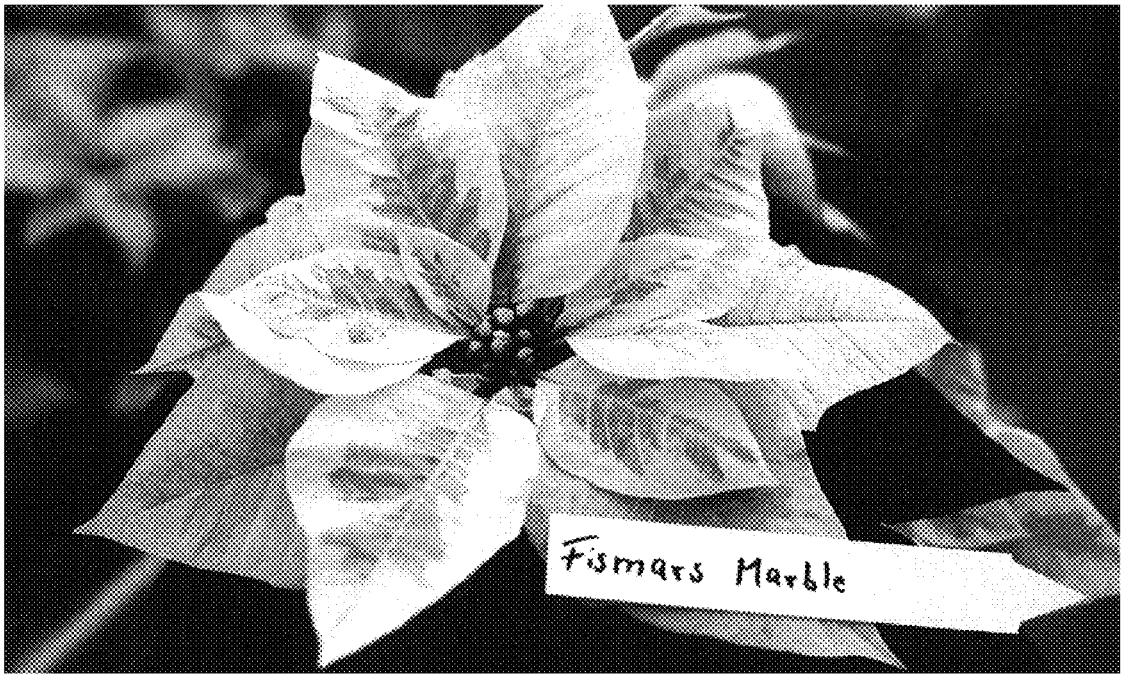
FIG. 2 shows a close-up of the mature inflorescences.

The following detailed description sets forth the distinctive characteristics of 'Fismars Marble'. The data which define these characteristics were collected from asexual reproductions carried out in Hillscheid, Germany. The plant history was taken on 18-week old plants which were planted as rooted cuttings in 14-cm pots on Jul. 28, 2005 and were pinched on Aug. 12, 2005, which left 7 to 8 leaves remaining. The plants were grown in a greenhouse at a minimum temperature of 18° C. and a ventilation temperature of 24° C. The plants initiated flowers under natural short-day conditions in fall. No black cloth was applied to the greenhouse to simulate short-day conditions. No growth regulator was applied. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:

*Family.*—Euphorbiaceae.

*Botanical.*—*Euphorbia pulcherrima* (Willd. Ex Klotzsch).

*Common name.*—Poinsettia.

Parentage: Mutation of the red-colored poinsettia plant 'Fismars' (U.S. Plant Pat. No. 14,977).

Growth:

*Form.*—Shrub, self-branching.

*Growth and branching habit.*—Compact to medium size; pinched plants are bushy and round in shape.

*Height* (*from soil line to the top*).—25.1 cm.

*Width.*—50.5 cm.

*Time to produce a finished flowering plant.*—About 17 weeks (the total cultivation time) for a 14-cm pot or 9 weeks after the autumnal equinox (late November) when marketable quality is reached.

*Time to initiate and develop roots.*—20 to 24 days in a greenhouse at 22° C. to 24° C.

Branches:

*Average number.*—7.0.

*Length of branches.*—20 cm to 22 cm.

*Internode length.*—1.0 cm to 2.5 cm.

*Diameter of branches.*—0.5 cm to 0.7 cm.

*Stem color.*—Mainly RHS 143A (green) but is RHS 144B (green) near the tips.

Leaves:

*Quantity.*—50 to 55 leaves per plant (7 to 8 leaves per branch).

*Arrangement.*—Alternate.

*Size.*—Length: 11.9 cm. Width: 9.0 cm.

*Shape.*—Ovate.

*Margin.*—Entire.

*Apex.*—Acuminate.

*Base.*—Mostly truncate or weakly rounded.

*Lobes.*—Very few, with rounded tips.

*Color* (*mature leaves*).—Upper surface: From RHS 137A to RHS 139A. Lower surface: RHS 137B.

*Color* (*immature leaves*).—Upper surface: RHS 143A. Lower surface: RHS 137D.

*Texture.*—Upper surface: Smooth and flat, only weakly veined. Lower surface: Flat and smooth, except for the slightly protruding midrib and finer side veins in a pinnate pattern.

*Venation color.*—Upper surface: RHS 144C (green). Lower surface: RHS 145B (pale green).

*Variegation.*—None.

*Leaf petiole.*—Length: 7.1 cm. Diameter: 0.3 cm. Color: Upper surface: RHS 145A (light-green). Lower surface: RHS 145B. Texture: Glabrous. Aspect: Horizontally directed or somewhat slanting downward, the leaves are pointed in the downward direction.

Bracts:

*Number per inflorescence.*—10 to 13.

*Shape.*—Ovate.

*Apex.*—Acuminate.

*Base.*—Truncate to rounded, smallest bracts are acute.

*Lobes.*—Very few, shallow and rounded.

*Size.*—Length: 13.5 cm. Diameter: 8.3 cm.

*Texture.*—Mostly smooth with younger bracts moderately rugose.

*Bract color.*—Upper surface: RHS 51D (light-pink) in the middle and RHS 4D or RHS 2D (yellowish-white) in the margin for larger bracts; RHS 51B (pink) in the middle and RHS 4D in the margin for younger bracts.

*Vein color.*—Upper surface: RHS 4D (pale yellowish-white). Lower surface: RHS 145D (pale green) or RHS 159A.

*Bract petiole.*—Length: Up to 1.7 cm. Color: Upper surface: RHS 151A to RHS 18D. Lower surface: RHS 37B (light salmon pink).

Inflorescence:

*Blooming habit.*—Beginning under natural short-day conditions in the Fall: Botanically (cyathia open): About December 1. Commercially (bracts colored, marketable): Late November.

*Inflorescence type.*—Medium to large size, mostly flat and parallel to the surface of the foliage canopy, with the bracts slightly convex, in the center is a cyme with 5 to 10 normal size cyathia.

*Average number of inflorescences.*—6.8.

*Lastingness.*—About 4 to 5 weeks with no dropping of bracts.

*Diameter.*—23 cm to 25 cm.

*Height.*—3.0 cm to 4.0 cm.

Cyme:

*Cyme diameter.*—1.5 cm to 2.0 cm.

*Cyathia number.*—5 to 10 in a tight cluster.

*Cyathium.*—Shape: Ovate. Diameter: 0.5 cm. Length: 0.6 cm to 0.7 cm. Color: Mainly RHS 144B (green); with RHS 51B (pink) weak spots or stripes; near RHS 159A (pale brown-orange) at top.

*Peduncle.*—Color: RHS 145B (light-green). Length: 0.3 cm.

*Nectar cups.*—Number: One or two per cyathium. Size: Up to 0.6 cm wide. Color: RHS 12A or RHS 13B (deep-yellow).

Reproductive organs:

*Stamens.*—Only occasionally developed. Number: 1 to 5 in a cluster. Filaments: Color: RHS 51D (light-pink). Length: 0.2 cm to 0.3 cm. Pollen: None observed.

Fruit and seed set: No seed set observed so far.

Disease and insect resistance: No particular resistance or susceptibility has been observed.

COMPARISON WITH PARENTAL AND COMMERCIAL CULTIVARS

'Fismars Marble' differs from the parental cultivar 'Fismars' (U.S. Plant Pat. No. 14,997) by having slightly convex, variegated pink bracts with cream margins instead of flat, red bracts. Additionally, 'Fismars Marble' develops few to no stamens while 'Fismars' has a normal number of stamens.

'Fismars Marble' differs from the commercial cultivar 'Fiscor Marble' (unpatented), by having deeper pink, shorter bracts as well as leaves with weaker lobes compared to 'Fiscor Marble'. Additionally, 'Fismars Marble' develops few to no stamens while 'Fiscor Marble' develops a normal number of stamens under the same growing conditions.

'Fismars Marble' differs from the commercial cultivar '490 Marble' (U.S. Plant Pat. No. 8,833) by having shorter and smoother bracts compared to '490 Marble' which has longer bracts that show distinct rugosity. Additionally, 'Fismars Marble' has a wider plant habit and a later flowering response compared to '490 Marble'.

I claim:

1. A new and distinct cultivar of Poinsettia plant as shown and described herein.

* * * * *